(12) United States Patent
Tien (10) Patent No.: US 7,055,527 B2
(45) Date of Patent: Jun. 6, 2006

(54) CUTICLE REMOVING DEVICE

(76) Inventor: Tien-Jen Tien, No.55-1, Lioujhih Lane, Lioufen Rd., Waipu-Township, Taichung County (TW) 438

( * ) Notice: Subject to any disclaimer, the term of this patent is extended or adjusted under 35 U.S.C. 154(b) by 221 days.

(21) Appl. No.: 10/612,854

(22) Filed: Jul. 3, 2003

(65) Prior Publication Data

US 2005/0000534 A1  Jan. 6, 2005

(51) Int. Cl.
*A45D 29/04* (2006.01)
*A45D 29/18* (2006.01)

(52) U.S. Cl. ..................... 132/75.6; 132/76.5
(58) Field of Classification Search ............... 132/76.4, 132/75.6, 73.5, 75, 150, 309–310, 76.5; 15/106, 15/105, 65, 164, 114, 160; 433/147; 81/177.4, 81/490, 489, 491, 461
See application file for complete search history.

(56) References Cited

U.S. PATENT DOCUMENTS

| | | | | |
|---|---|---|---|---|
| 5,331,707 A | * | 7/1994 | Irizarry | 15/167.1 |
| 5,491,863 A | * | 2/1996 | Dunn | 15/106 |
| 5,709,003 A | * | 1/1998 | Batch | 15/106 |
| 5,765,253 A | * | 6/1998 | Martinez | 15/160 |
| 6,142,156 A | * | 11/2000 | Brunderman | 132/76.4 |
| 6,629,478 B1 | * | 10/2003 | Kozak | 81/490 |

* cited by examiner

*Primary Examiner*—John J. Wilson
*Assistant Examiner*—Robyn Doan
(74) *Attorney, Agent, or Firm*—Alan D. Kamrath; Nikolai & Mersereau, P.A.

(57) ABSTRACT

A cuticle removing device includes a first set having a first handle and a first scrubbing stick connected to a first end of the first handle. A recess is defined in the first handle and communicates an opening defined in a second end of the first handle. A second set has a second handle and a second scrubbing stick connected to a first end of the second handle. The second set is removably received in the recess. A ring is mounted to an outer periphery of the second handle and engaged with an inner periphery of the recess.

6 Claims, 9 Drawing Sheets

CUTICLE REMOVING DEVICE

FIELD OF THE INVENTION

The present invention relates to a cuticle removing device which includes a handle and a scrubbing stick, wherein a small cuticle removing device is removably inserted in a recess in the handle.

BACKGROUND OF THE INVENTION

Figure 9:
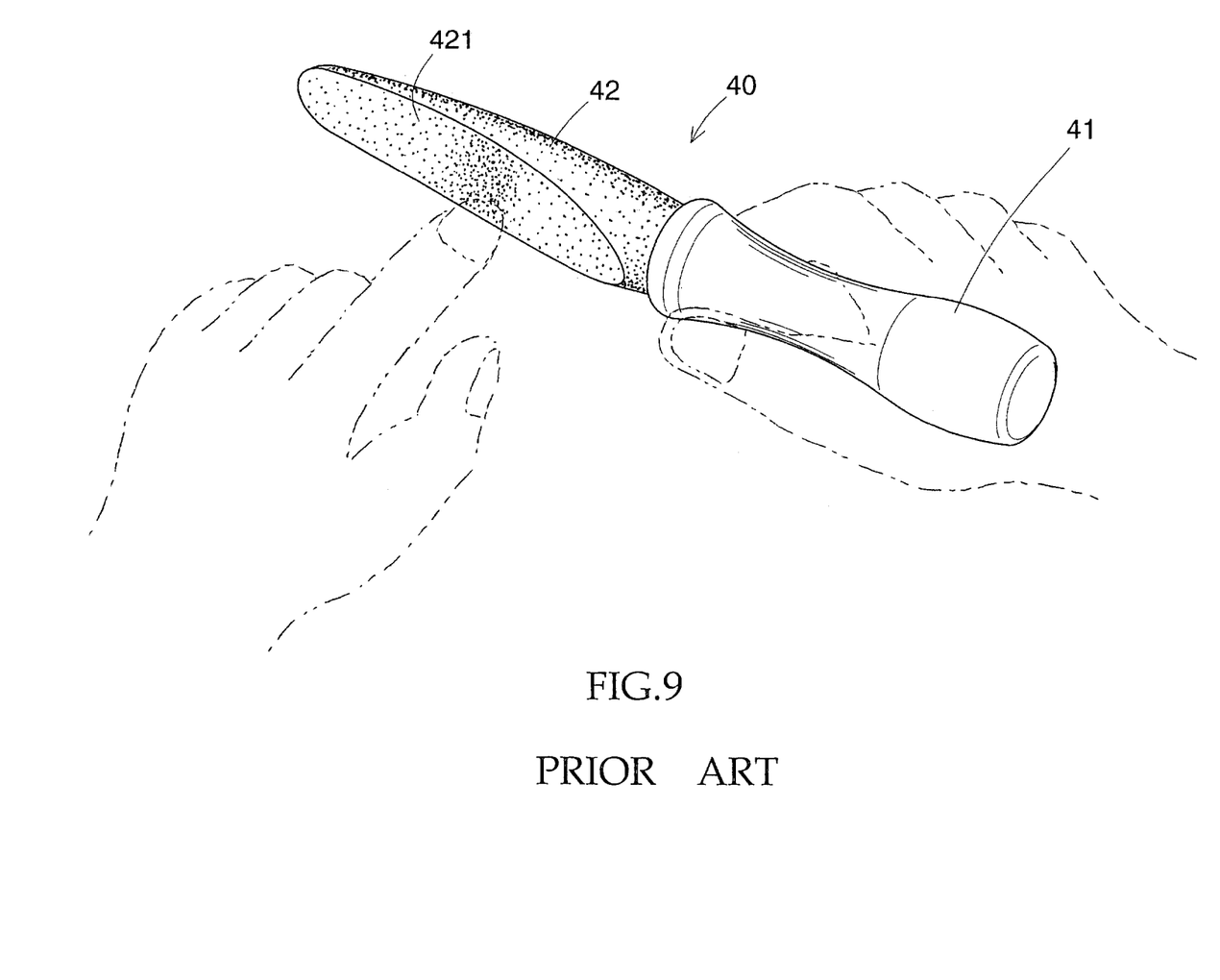
FIG. 9 is a perspective view of the cuticle removing device of the present invention of a conventional cuticle removing device.

A conventional cuticle removing device 40 is disclosed in FIG. 9 and generally includes a handle 41 and a scrubbing stick 42 which is connected to the handle 41. The scrubbing stick 42 includes a scrubbing surface 421 so that a user may hold the handle 41 and remove the cuticle of limbs by moving the scrubbing stick 42 on the area of the limbs by the scrubbing surface 421. The size of the scrubbing stick 42 is fixed, and it is designed for using on a large area, so that it is not convenient when being used onto a small area. The users then have to prepare another cuticle removing device which is designed for small areas.

The present invention intends to provide a cuticle removing device that includes a large set and a small set which is received in the handle of the large set so that the user may easily store and carry the device.

SUMMARY OF THE INVENTION

In accordance with one aspect of the present invention, a cuticle removing device includes a first set and a second set. Each of the two sets has a handle and a scrubbing stick. The handle of the first set has a recess in which the second set is removably received. The handle of the second set has a ring mounted thereto, and the ring is engaged with an inner periphery of the recess of the handle of the first set.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
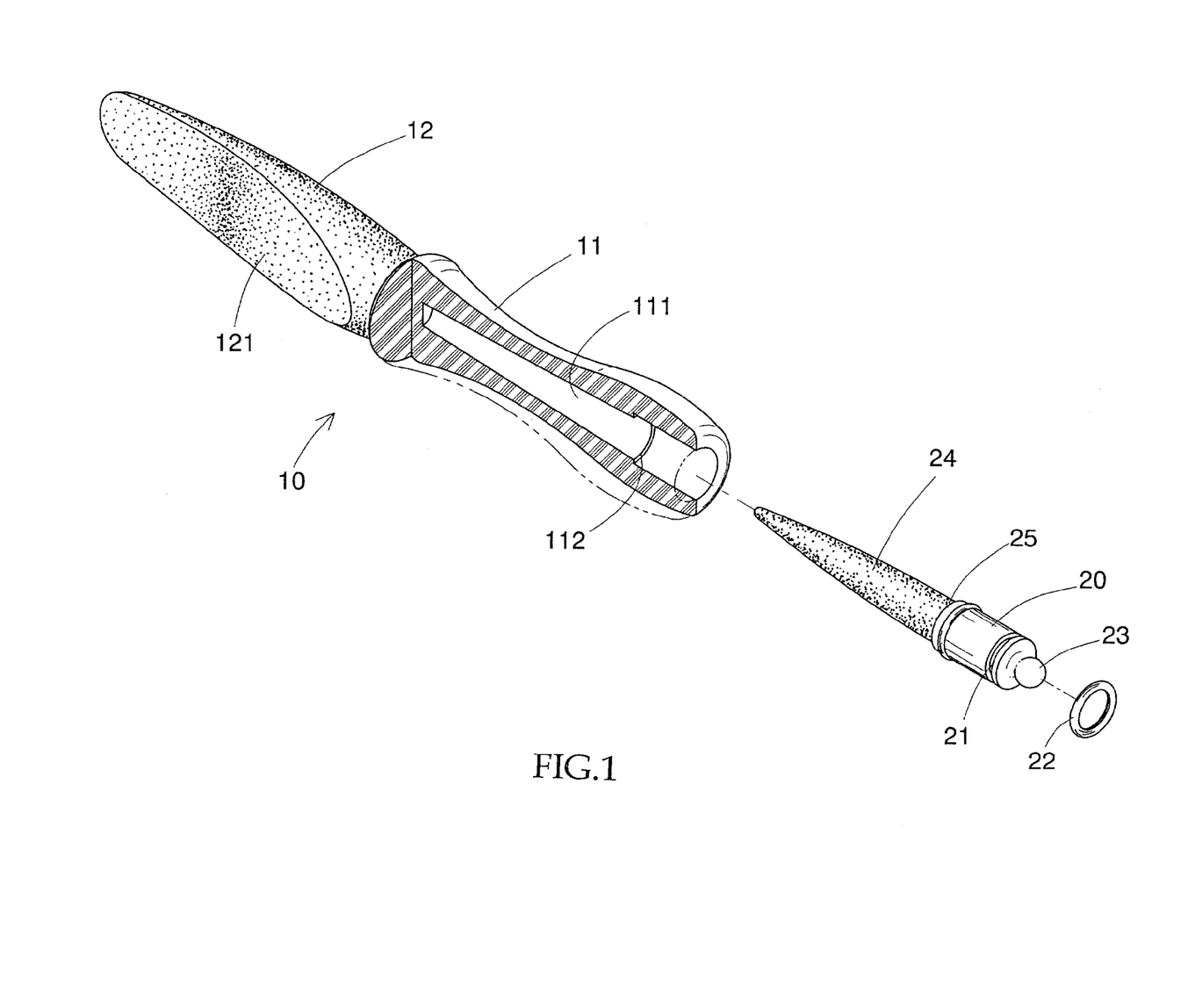
FIG. 1 is an exploded view of the cuticle removing device of the present invention.
Figure 2:
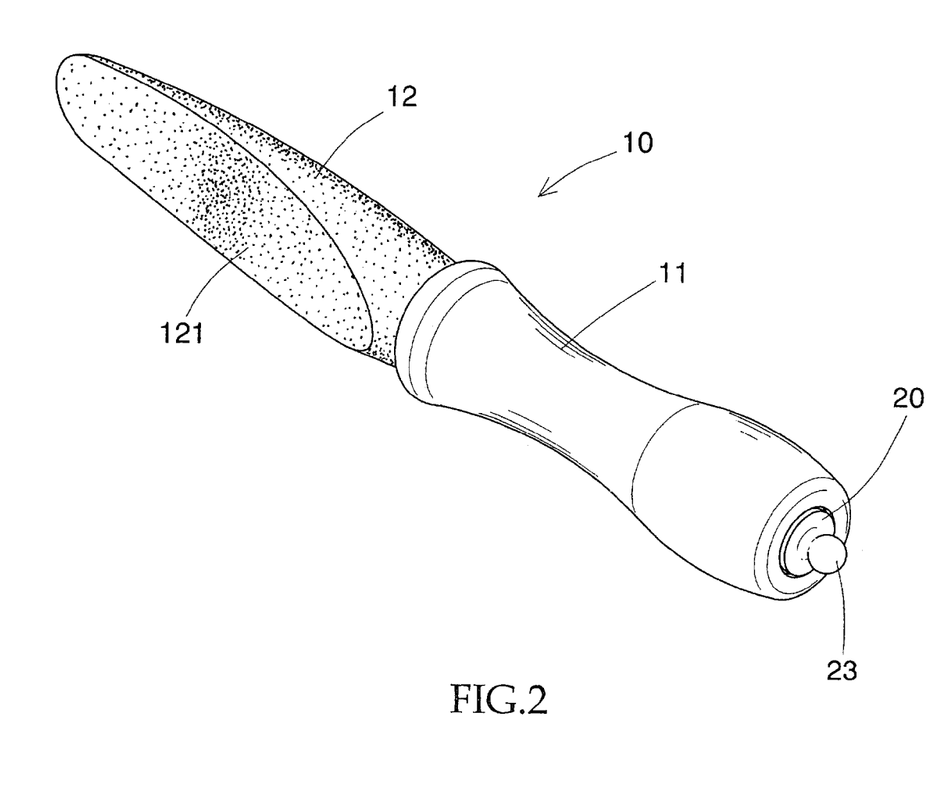
FIG. 2 is a perspective view of the cuticle removing device of the present invention.
Figure 3:
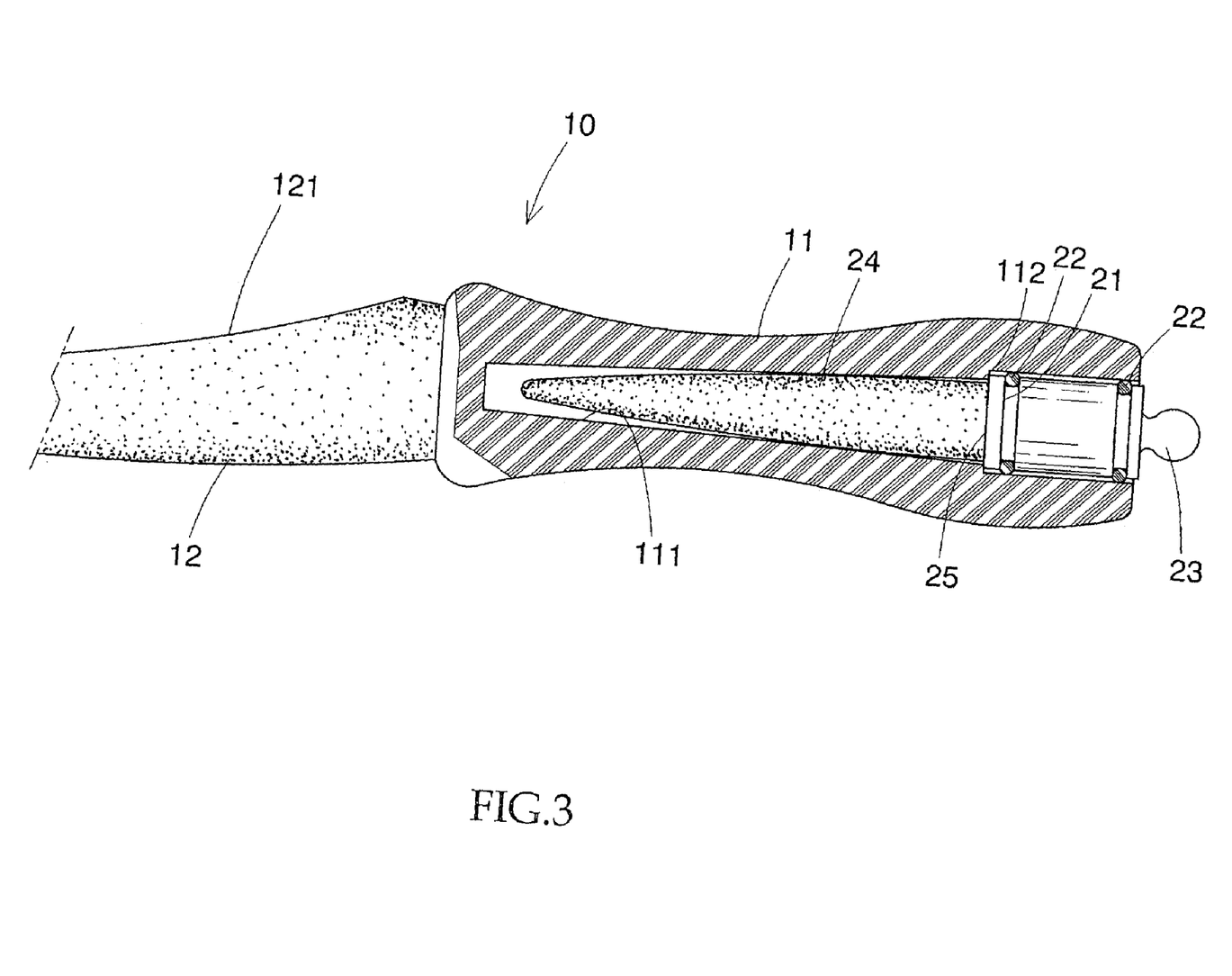
FIG. 3 is a cross sectional view of the cuticle removing device of the present invention showing the second set received in the recess of the handle of the first set.

Referring to FIGS. 1 to 3, the cuticle removing device 10 of the present invention comprises a first set having a first handle 11 and a first scrubbing stick 12 which is connected to a first end of the first handle 11. A scrubbing area 121 is defined in an outer periphery of the first scrubbing stick 12. A recess 111 is defined in the first handle 11 and communicates an opening defined in a second end of the first handle 11. The recess 111 includes a first section and a second section. An annular step 112 is defined between the first section and the second section in the inner periphery of the recess 111.

A second set has a second handle 20 and a second scrubbing stick 24 which is connected to a first end of the second handle 20. A diameter of the second handle 20 is larger than that of the second scrubbing stick 24 so that a shoulder 25 is formed on an end surface of the first end of the second handle 20. The second set is removably received in the recess 111, wherein the second scrubbing stick 24 is received in the first section of the recess 111 and the second handle 20 is received in the second section of the recess 111. The shoulder 25 is engaged with the annular step 112.

A knob 23 is connected to a second end of the second handle 20 and extends beyond the second end of the first handle 11. A groove 21 is defined in the outer periphery of the second handle 20, and a ring 22 is engaged with the groove 21. The ring 22 protrudes from the outer periphery of the second handle 20 and is engaged with the inner periphery of the recess 111 so that the second set is positioned in the recess 111.

Figure 4:
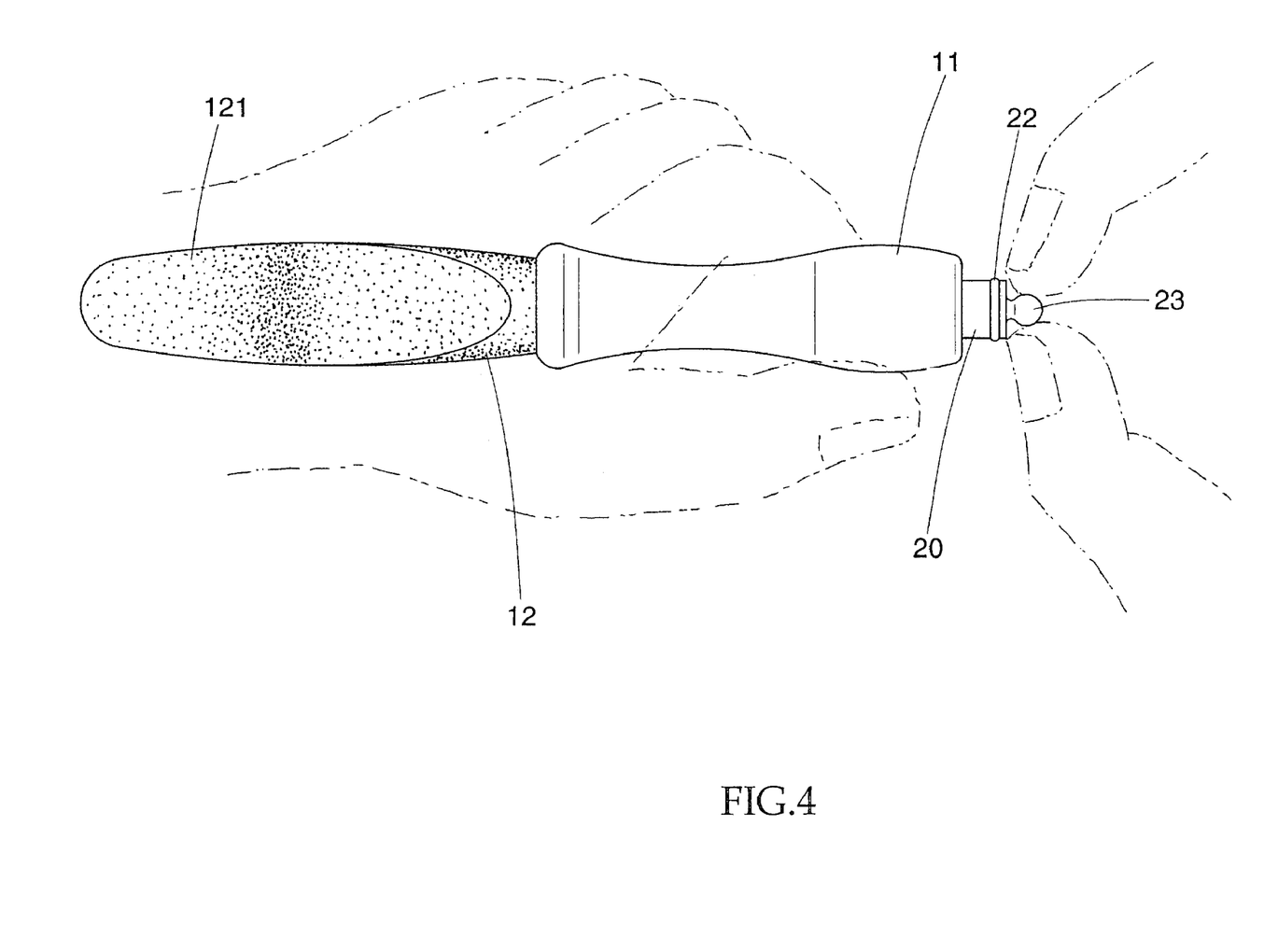
FIG. 4 is an elevational view of the cuticle removing device of the present invention showing that the user may pull the second set from the handle of the first set.
Figure 5:
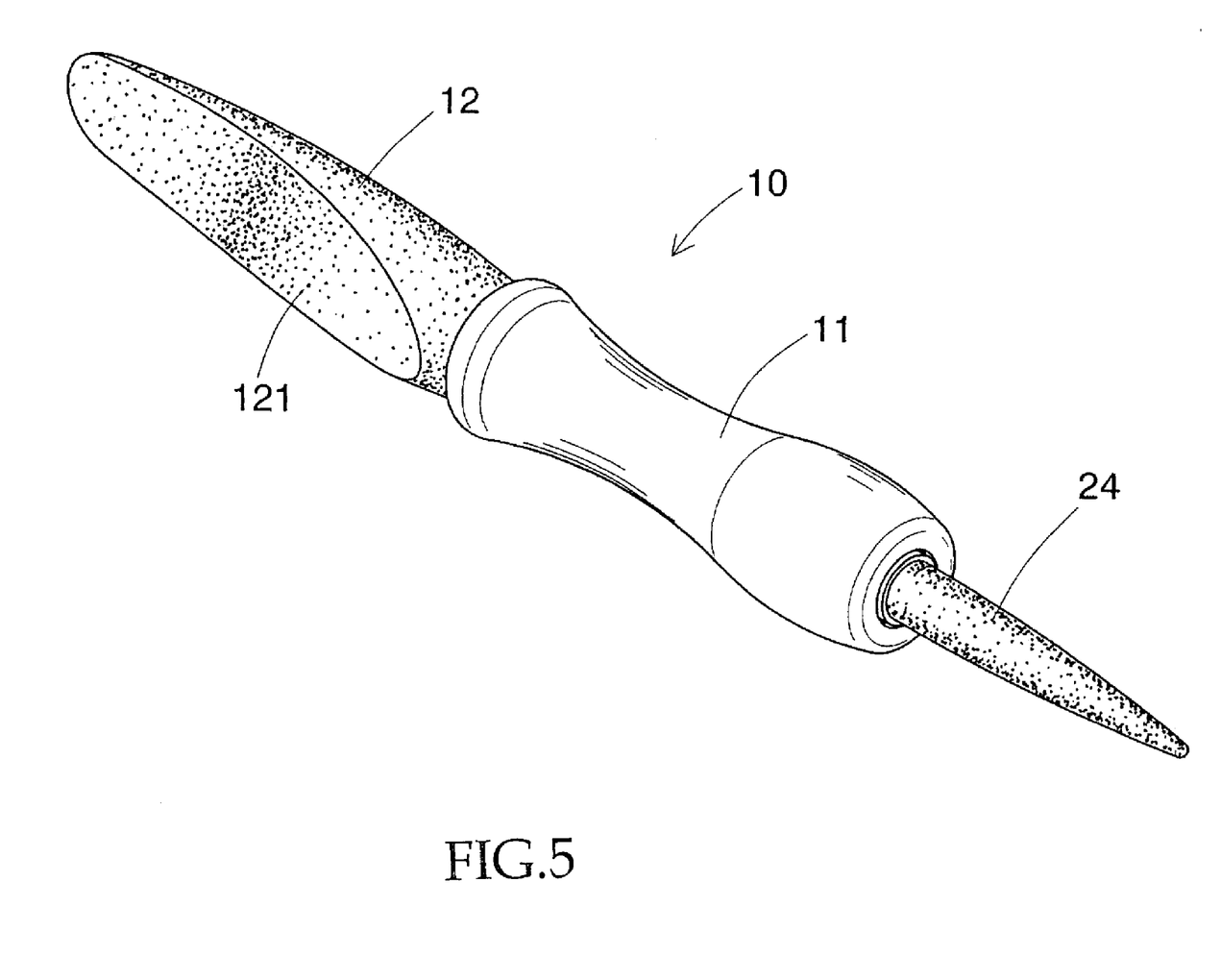
FIG. 5 is a perspective view of the cuticle removing device of the present invention with the handle of the second set engaged with the recess of the handle of the first set and with the scrubbing stick extending out from the handle of the first set.
Figure 6:
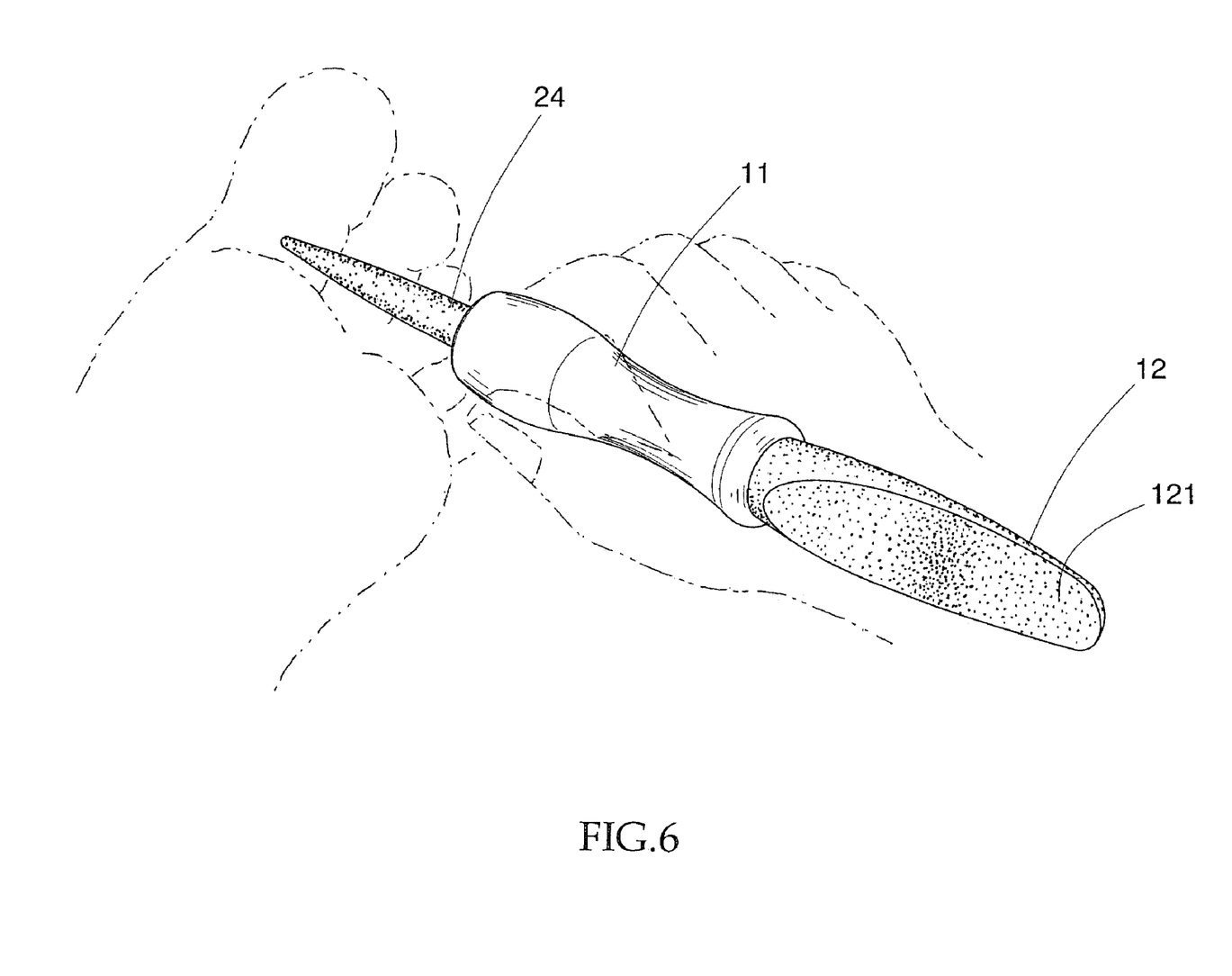
FIG. 6 is a perspective view of the cuticle removing device of the present invention showing the use of the scrubbing stick of the second set.

Referring to FIGS. 4 to 6, the user may hold the knob 23 and pull the second set from the first handle 11. The second handle 20 is then able to be inserted in the second section of the recess 111, and the second scrubbing stick 24 extends out from the second end of the first handle 11. Therefore, the user may hold the first handle 11 to use the two scrubbing sticks 12, 24 as needed.

Figure 7:
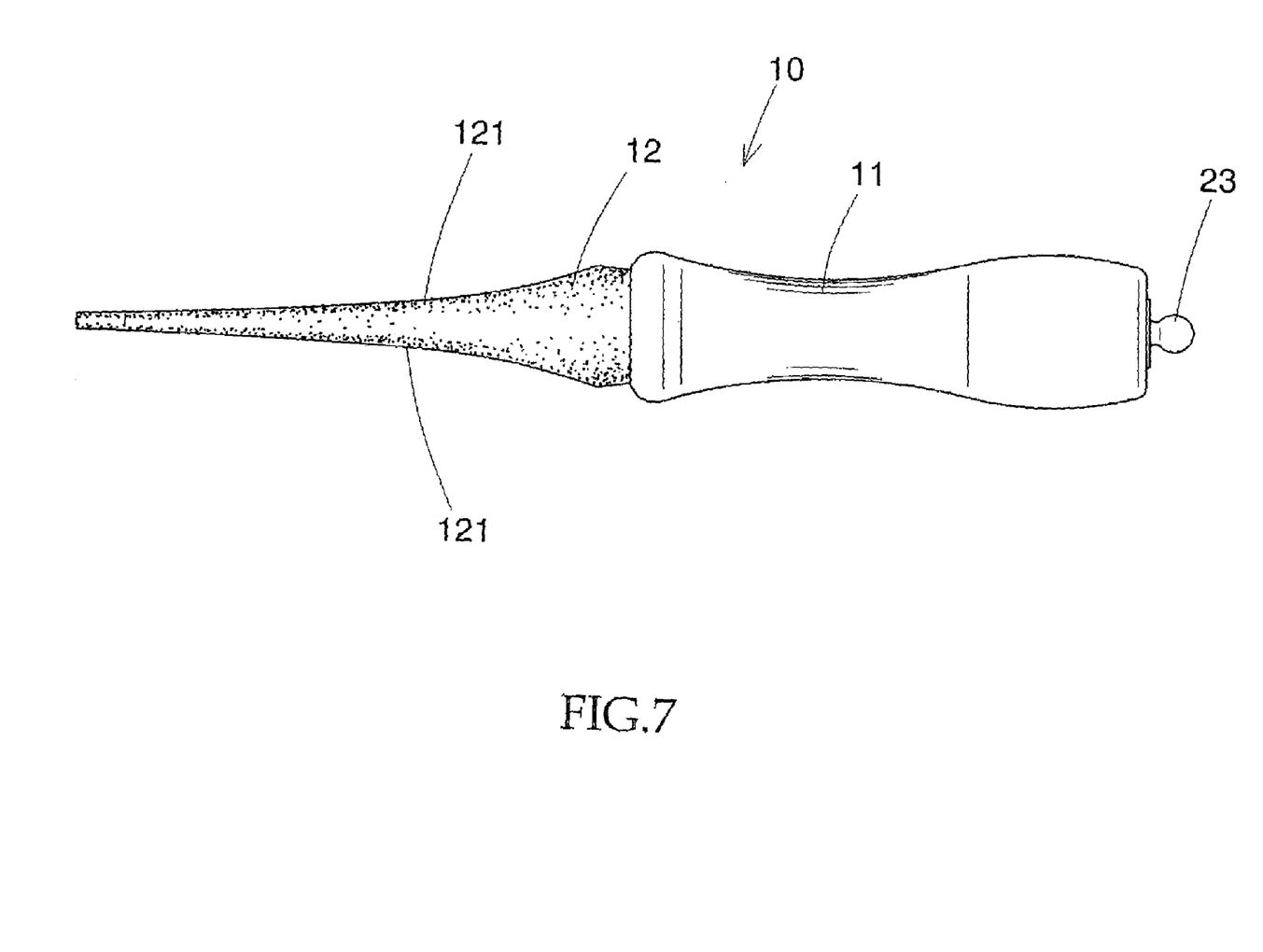
FIG. 7 is a elevational view of the cuticle removing device of the present invention showing that the scrubbing stick of the first set includes two scrubbing areas.
Figure 8:
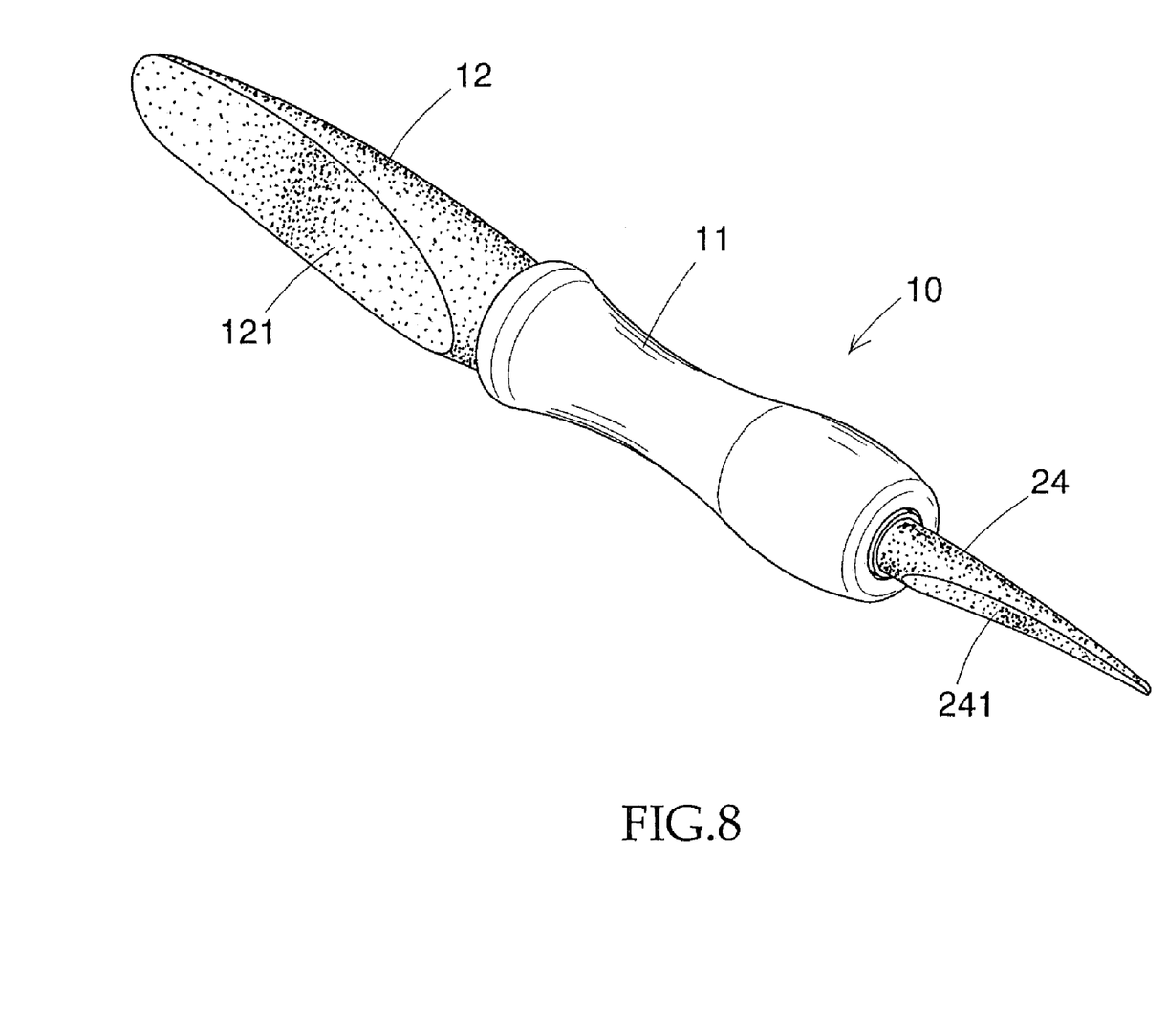
FIG. 8 is a perspective view of the cuticle removing device of the present invention showing each of the two scrubbing sticks has only one scrubbing areas.

FIG. 7 shows the first scrubbing stick 12 of the first set including two scrubbing areas 121. FIG. 8 shows that each of the two scrubbing sticks 12, 24 has only one scrubbing area 121/241.

While we have shown and described the embodiment in accordance with the present invention, it should be clear to those skilled in the art that further embodiments may be made without departing from the scope of the present invention.

What is claimed is:

1. A cuticle removing device comprising: a first set having a first handle and a first scrubbing stick which is connected to a first end of the first handle, a recess defined in the first handle and communicating an opening defined in a second end of the first handle, and a second set having a second handle and a second scrubbing stick which is connected to a first end of the second handle, with the second handle being of a size and shape for slideable engagement with the recess, with the second set being sized and shaped allowing removal of the second set from the recess, allowing the second scrubbing stick to be received in the recess while the second handle is engaged with the recess and allowing the second scrubbing stick to be outside the recess while the second handle is engaged with the recess, wherein a diameter of the second handle is larger than that of the second scrubbing stick so that a shoulder is formed on an end surface of the first end of the second handle, the recess including a first section for receiving the second scrubbing stick and a second section for receiving the second handle of the second set, an annular step defined between the first section and the second section, the shoulder engaged with the annular step.

2. The device as claimed in claim 1, wherein a knob is connected to a second end of the second handle and extends beyond the second end of the first handle.

3. A cuticle removing device comprising: a first set having a first handle and a first scrubbing stick which is connected to a first end of the first handle, a recess defined in the first handle and communicating an opening defined in a second end of the first handle, and a second set having a second handle and a second scrubbing stick which is connected to a first end of the second handle, with the second handle being of a size and shape for slideable engagement with the recess, with the second set being sized and shaped allowing removal of the second set from the recess, allowing the second scrubbing stick to be received in the recess while the second handle is engaged with the recess and allowing the second scrubbing stick to be outside the recess while the second handle is engaged with the recess, wherein a groove is defined in the outer periphery of the second handle and a ring is engaged with the groove.

4. The device as claimed in claim 3, wherein a knob is connected to a second end of the second handle and extends beyond the second end of the first handle.

5. A cuticle removing device comprising: a first set having a first handle and a first scrubbing stick which is connected to a first end of the first handle, a recess defined in the first handle and communicating an opening defined in a second end of the first handle, and a second set having a second handle and a second scrubbing stick which is connected to a first end of the second handle, with the second handle being of a size and shape for slideable engagement with the recess, with the second set being sized and shaped allowing removal of the second set from the recess, allowing the second scrubbing stick to be received in the recess while the second handle is engaged with the recess and allowing the second scrubbing stick to be outside the recess while the second handle is engaged with the recess, with the device further comprising a ring mounted to an outer periphery of the second handle and engaged with an inner periphery of the recess.

6. The device as claimed in claim 5, wherein a knob is connected to a second end of the second handle and extends beyond the second end of the first handle.

* * * * *